United States Patent [19]

Grimsby

[11] Patent Number: 4,620,910
[45] Date of Patent: Nov. 4, 1986

[54] PROCESS FOR THE PRODUCTION OF DICHLOROHYDRINS

[75] Inventor: F. Norman Grimsby, Houston, Tex.

[73] Assignee: Shell Oil Company, Houston, Tex.

[21] Appl. No.: 814,331

[22] Filed: Dec. 27, 1985

[51] Int. Cl.$^4$ ............................................. B01D 51/02
[52] U.S. Cl. .............................. 204/182.4; 204/182.3; 204/81
[58] Field of Search ............... 204/182.3, 182.4, 182.5, 204/81

[56] References Cited

U.S. PATENT DOCUMENTS 3,909,382 9/1975 Mueller et al. .................. 204/182.4

Primary Examiner—R. L. Andrews
Attorney, Agent, or Firm—Ronald R. Reper

[57] ABSTRACT

A continuous process for the production of dichlorohydrin by the reaction of allyl chloride, water and chlorine in a reaction zone comprising a plurality of reaction stages, wherein the aqueous reaction product from each stage, except the final stage is electrodialyzed and the diluate is passed to a subsequent reaction stage.

4 Claims, 1 Drawing Figure

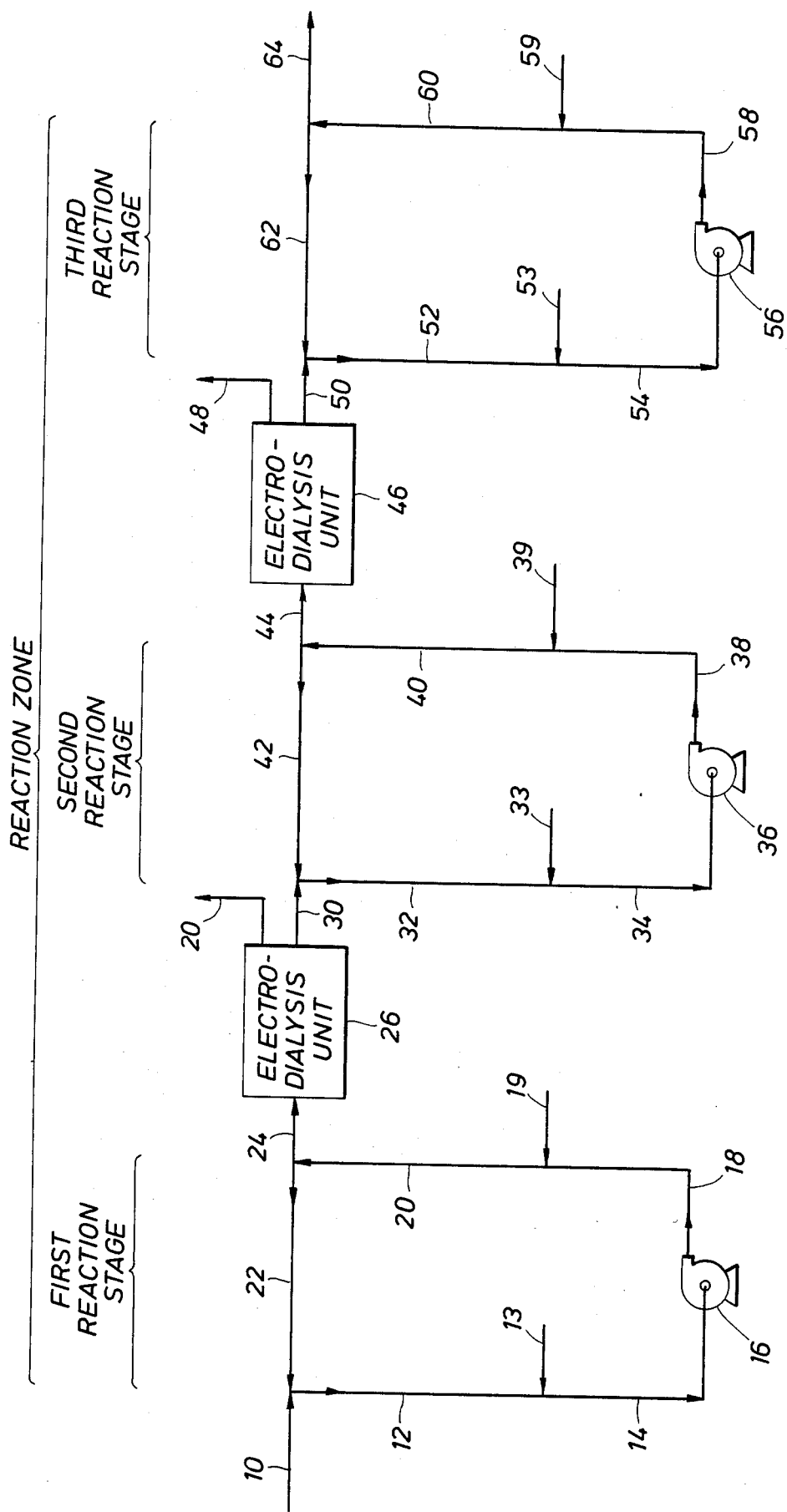

PROCESS FOR THE PRODUCTION OF DICHLOROHYDRINS

BACKGROUND OF THE INVENTION

It is known to prepare an aqueous solution of dichlorohydrins e.g., 2,3 dichloro-1-propanol and 1,3 dichloro-1-propanol, herein collectively dichlorohydrin, by reacting in a reaction zone allyl chloride, water and chlorine in dilute aqueous phase.

U.S. Pat. No. 2,714,121, incorporated herein by reference, discloses producing halohydrins by using high dilution of e.g., 250 to 400 volumes of water per volume of e.g., a halosubstituted hydrocarbon in aqueous medium with subsequent addition of the halogen, and keeping the organic by-product phase dispersed as fine particles.

U.S. Pat. No. 2,714,123, incorporated herein by reference, discloses producing an aqueous solution of dichlorohydrin in a series of reaction zones wherein substantially all of the water is fed to the first of the reaction zones and the other reactants added in substantially equimolar proportions into each of the other reaction zones.

U.S. Pat. No. 3,909,382 discloses recovering acid values, such as hydrochloric acid formed during olefin chlorohydrination, by series flow through a plurality of electrodialysis stages to upgrade the acid to higher concentration.

From Japanese Pat. No. 74,00369 it is known that the product mixture from the reaction of a lower olefin, chlorine and water can be electrodialyzed to remove the by-product ions of hydrogen and chlorine, and the ion-depleted chlorohydrin solution circulated to the single reaction zone, enabling the production of a concentrated aqueous chlorohydrin solution.

A disadvantage of the known processes is that substantial amounts of water are used in the reaction zone of the process to obtan higher selectivity, that is the yield of the desired chlorohydrin product, based upon the chemical feed. Such conventional processes result in a substantial volume of aqueous effluent containing minor amounts e.g., 1000 to 2000 parts per million by weight (ppmn) of organic impurities. Such effluent requires energy intensive treatment to reduce the amount of organic materials to low levels acceptable to be passed to receiving bodies of water such as rivers, lakes and the like. The present invention provides a method for both improving selectivity to the desired dichlorohydrin product and enabling reduction in the amount of aqueous effluent, thereby effecting great energy savings for the overall process.

SUMMARY OF THE INVENTION

According to the invention, there is provided in a continuous process for the production of an aqueous solution of dichlorohydrin by the reaction of allyl chloride, water and chlorine in a reaction zone comprising a plurality of reaction stages arrayed in series flow, the method for improving selectivity which comprises electrodialyzing a significant part of the reaction mixture from each stage, except the final reaction stage, in a separate electrodialysis zone, to afford (1) a concentrate stream having higher chloride content than the reaction mixture feed to each said electrodialysis zone, and (2) a diluate stream containing the dichlorohydrin and having a lower chloride content than said feed to each said electrodialysis zone removing each concentrate stream from the reaction zone, and passing each diluate stream to a subsequent reaction stage.

THE DRAWING

The FIGURE depicts a schematic flow diagram of a preferred embodiment of the invention.

DESCRIPTION OF PREFERRED EMBODIMENTS

In the principal reaction, allyl chloride is converted to a mixture of the two isomers of glycerol dichlorohydrin by reaction with hypochlorous acid, HClO, which is readily formed when chlorine is dissolved in water. The dichlorohydrination reaction takes place readily at temperatures in the range from about 15° to about 50° C. Decreased temperature rapidly increases the amount of dissolved chlorine as well as the concentration of the hypochlorous acid. For maximum chlorohydrin yield it is necessary to run the reaction at low concentration, of chloride ion and of chlorohydrin, i.e., with high water dilution to avoid the formation of undesired by-product e.g., trichloropropane and tetrachloropropyl ether.

Electrodialysis is by now a well established industrial process. Basically, an electrodialysis unit comprises a plurality of membranes alternately anionic and cationic placed between an anode and a cathode connected to a direct current source. The membranes are usually separated from each other by 1 to 5 mm using appropriate spacers and the feed stream may be made to flow through a spacer creating a turbulent path in order to increase turbulence of the liquids contacting the membranes or insheet-type flow to reduce pumping pressure. The construction of the unit is generally in the form of a stack, like a filter stack. The membranes which usually contain ion exchange groups have a fixed positive or negative charge. The cationic membranes have negative fixed charges; the anionic membranes have positive fixed charges. Electrical neutrality in the membrane matrix is satisfied by the migrating cations (through cationic membranes) and anions, (through anionic exchange membranes).

If a feed stream is introduced uniformly from the top of the electrodialysis unit, it will be found that passages in the unit having an anion membrane on the cathode side of the passage and vice versa will become concentrate streams richer in ionized (herein saline) components and the other streams in passages bounded by anion membranes on the anode side and cathode membranes on the cathode side will become depleted in ionized components. Such depleted stream or streams are herein referred to as the diluate stream.

When a direct current is applied across the two electrodes (anode and cathode) anions will tend to migrate towards the anode passing through the anion exchange membrane and being stopped by the first cation exchange membrane. In like manner, cations will cross through the cationic exchange membrane and will be stopped by the anionic exchange membranes. However, non-electrolyte species are not prevented from passing through the exchange membranes, except in so far as these are made of a tighter pore structure, even so, however, non-electrolytes will migrate through the membranes, the actual amount of migration depending on relative volume of diluate/concentrate streams.

The anionic and cationic membranes employed herein are known in the art. Generally, the anionic and cationic membranes comprise flat sheets of inorganic or organic materials which have extreme water-insolubility. Preferably the anionic and cationic membranes are prepared from synthetic organic resinous, polymeric materials, (e.g., polystyrene polymers) to which are bonded ionic groups. Any strong or weak base (e.g., tertiary amines or quaternary ammonium compounds) can be chemically bonded to the organic material to form cationic membranes; any strong or weak acid (e.g., aryl sulfonates) can be chemically bonded to the organic resinous material to form anionic membranes.

Generally, the anionic and cationic membranes herein, either in the form of laminate or a homogeneous cast or sheet, are "backed" or reinforced with an imbedded screen or matrix of synthetic reinforcing fabric, for example, fiberglass to provide them with a substantially rigid structure. Other 'backings' can be used, provided the anionic and cationic membranes remain essentially impervious to mass flow but porous enough to permit ion migration or transfer.

The cation and anion-exchange membranes can be any cation- and anion-selective membranes respectively which are essentially stable in the feed water and not chemically degraded by the components therein. Exemplary membranes are disclosed in the article entitled "Electrodialysis", Kirk-Othmer, Encyclopedia of Science and Technology, pages 846-865 (Second Edition, Interscience Publishers, 1965) and U.S. Pat. Nos. 2,730,768, 2,762,272 2,860,097 and 3,616,385 incorporated herein by reference.

Generally, for stability of the membranes, it is necessary to employ temperatures below about 70° C. during electrodialysis. While in terms of electrical efficiency it would be preferred to carry out the electrodialysis step at about 55° C., especially at a temperature in the range from about 20° to 50° C.

The diluate stream after the electrodialysis step has greatly reduced ion content and is passed to the next reaction stage.

The concentrate stream from the several electrodialysis zones may be handled separately or combined resulting in a aqueous stream of relatively small volume for subsequent treatment or disposal.

An embodiment of the invention will be described with reference to the FIGURE which shows diagrammatically a preferred assemblage according to the invention. In the FIGURE a fresh water stream is continuously introduced through conduit 10 at a rate of about 142 gpm into a first-stage reaction loop comprising conduits 12, 14 pump 16, conduits 18, 20 and 22. Allyl chloride is continuously fed into the aqueous stream through conduit 13, while chlorine in an amount substantially equimolar with respect to the allyl chloride is fed to the first-stage reaction loop via conduit 19 at a rate of about 2 gpm. The reaction mixture is circulated through the loop at a rate of about 250 times the volume of allyl chloride added, and a portion of the mixture after passing through pump 16 is continuously diverted via conduit 24 to a first electrodialysis zone 26. The first-stage reaction effluent containing about 0.13 molar dichlorohydrin and 0.2N HCl is fed to an electrodialysis unit 26 comprised of alternating anionic exchange membranes designated as 203 QZL and cationic exchange membranes designated as 61CZL-386, which membranes are available from Ionics, Inc., Watertown, Mass. In general, the voltage across each stack of membranes is arranged so that there is a voltage of about 0.5 to 3.0 volts per cell pair, with a voltage of about 0.5 to about 1.0 volt being preferred. A concentrate stream of about 4N HCl is removed via conduit 28 for further treatment and/or disposal. From said first-stage electrodialysis zone 26 a diluate stream comprising about 0.13M dichlorohydrin and 0.0N HCl is passed via conduit 30 to second reaction stage, a like reaction loop. This second-stage reaction loop comprises conduits 32, 34 pump 36 and conduits 38, 40 and 42. Allyl chloride is continuously fed into the aqueous reaction mixture through conduit 33, and a substantially equimolar amount of chlorine through conduit 39. This reaction mixture too is circulated at a rate of about 250 times the volume of the allyl chloride added. A portion of the reaction mixture containing about 0.26M dichlorohydrin and about 0.14N HCl is diverted via conduit 44 to second electrodialysis zone 46. The conditions in the second electrodialysis zone are substantially like those in the first-stage electrodialysis zone resulting in removal of a concentrate stream of hydrochloric acid via conduit 48. The diluate stream containing about 0.01N hydrochloric is passed via conduit 50 to the third-stage reaction loop comprising conduits 52, 54 pump 56 conduits 58, 60 and 62. As with the previous reaction stages, allyl chloride and chlorine are added in substantially equimolar amounts via conduits 53 and 59 respectively. A portion of the reaction mixture containing about 0.4M dichlorohydrin and about 0.4N hydrochloric acid is removed via conduit 64 for conversion to derivatives such as epichlorohydrin and/or glycerine. it is found that approximately 94.9% of the entire amount of allyl chloride charged to the system is converted to dichlorohydrin, compared to about 91.6% w in a like system without the interstage electrodialysis units for an approximate 3% selectivity improvement.

As will be appreciated by those skilled in the art, the present process may be readily applied to an existing multistage process producing dichlorohydrin. The use of interstage electrodialysis enables flexibility of operation whereby as an alternate to improved selectivity. The use of lower amounts of fresh water feed to the process will enable an increase in dichlorohydrin productin capacity of up to 50% of original design, while gaining at least about 1-3% selectivity advantage. Yet another alternative is to maintain the same production rate and selectivity of the original design, but to lower operating costs such as steam requirements and effluent treatment costs by as much as one third, owing to the reduced fresh water requirements.

What is claimed is:

1. In a continuous process for the production of an aqueous solution of dichlorohydrin by the reaction of allyl chloride, water and chlorine in a reaction zone comprising a plurality of reaction stages arrayed in series flow, the method for improving selectivity which comprises electrodialyzing a significant part of the reaction mixture from each stage, except the final reaction stage, in a separate electrodialysis zone to afford (1) a concentrate stream having higher chloride content than the reaction mixture feed to each said electrodialysis zone, and (2) a diluate stream containing the dichlorohydrin and having a lower chloride content than said feed to each said electrodialysis zone; removing each concentrate stream from the reaction zone, and passing each diluate stream to a subsequent reaction stage.

2. A process as in claim 1 wherein the reaction zone comprises a series of at least three reaction stages.

3. A process as in claim 2 wherein the reaction zone comprises a series of from three to five reaction stages.

4. A process as in claim 1 wherein in the electrodialyzing step the voltage across each stack of cell pairs is between about 0.5 and 3.0 volts per cell pair.

* * * * *